United States Patent [19]

Goedde et al.

[11] Patent Number: 4,740,599

[45] Date of Patent: Apr. 26, 1988

[54] SYNTHESIS OF ALKYLSULFINYL SUBSTITUTED 2-PHENYLIMIDAZO(4,5-C)PYRIDINES

[75] Inventors: Jane A. Goedde; James M. Greene, both of Indianapolis, Ind.

[73] Assignee: Eli Lilly and Company, Indianapolis, Ind.

[21] Appl. No.: 915,287

[22] Filed: Oct. 3, 1986

[51] Int. Cl.$^4$ .......................................... C07D 471/04
[52] U.S. Cl. .................................................. 546/118
[58] Field of Search ........................................ 546/118

[56] References Cited

U.S. PATENT DOCUMENTS

| | | | |
|---|---|---|---|
| 3,985,891 | 10/1976 | Kutter et al. | 546/118 |
| 4,299,834 | 11/1981 | Austel et al. | 546/118 |
| 4,477,454 | 10/1984 | Jonas et al. | 546/118 |
| 4,568,680 | 2/1986 | Austel et al. | 546/118 |

FOREIGN PATENT DOCUMENTS

| | | | |
|---|---|---|---|
| 72926 | 3/1983 | European Pat. Off. | 546/118 |
| 79083 | 5/1983 | European Pat. Off. | 546/118 |
| 93593 | 11/1983 | European Pat. Off. | 546/118 |
| 3346602 | 6/1985 | Fed. Rep. of Germany | 546/118 |
| 0021375 | 7/1980 | Japan | 546/118 |

*Primary Examiner*—Henry R. Jiles
*Assistant Examiner*—J. Richter
*Attorney, Agent, or Firm*—Charles W. Ashbrook; Leroy Whitaker

[57] ABSTRACT

The present invention provides a process for preparing alkylsulfinyl 2-phenylimidazo[4,5-c]pyridines comprising reacting an N-(3-amino-4-pyridinyl)alkylthiobenzamide with an oxidizing agent in a lower alkanoic acid solvent.

6 Claims, No Drawings

SYNTHESIS OF ALKYLSULFINYL SUBSTITUTED 2-PHENYLIMIDAZO(4,5-C)PYRIDINES

BACKGROUND OF THE INVENTION

Substituted 2-phenylimidazo[4,5-c]pyridines are known. The compounds are useful as inotropic agents, anticoagulants, bronchodilators, and vasodilators. One especially useful class of 2-phenylimidazo[4,5-c]pyridines are those in which the phenyl moiety is substituted with an alkylsulfinyl group.

Such compounds generally are prepared by cyclizing an N-(3-amino-4-pyridinyl)alkylthiobenzamide to an alkylthio substituted phenylimidazo[4,5-c]pyridine. This cyclization step often occurs under extreme conditions, such as refluxing POCl$_3$, or POCl$_3$ in pyridine. After cyclization, the alkylthio group is oxidized to the required alkylsulfinyl moiety using entirely different reaction conditions.

European Patent Application No. 93,593 is representative of the typical two step process used to produce such compounds. The reference describes reacting a 3,4-diamino pyridine with an alkylthio substituted benzoic acid or benzoic acid derivative to form an alkylthio substituted 2-phenylimidazo[4,5-c]pyridine, followed by oxidation of the alkylthio group to an alkylsulfinyl group. The cyclization reaction is preferably conducted in dehydrating agents such as polyphosphoric acid or phosphorus oxychloride, while the oxidation reaction requires an oxidizing agent such as m-chloroperbenzoic acid, t-butylhypochlorite, or hydrogen peroxide.

The prior art fails to suggest the use of an oxidizing agent in an alkanoic acid to effect cyclization and oxidation of N-(3-amino-4-pyridinyl)alkylthiobenzamides to alkylsulfinyl 2-phenylimidazo[4,5-c]pyridines. The present invention provides a process which employs an oxidizing agent in an alkanoic acid to perform both the cyclization and oxidation steps. The invention thus obviates the need to isolate intermediates, since both steps employ the same reaction conditions. In addition, the cyclization portion of the present process is more facile than previously disclosed cyclization reactions, thus allowing the process to be conducted under milder reaction conditions.

SUMMARY OF THE INVENTION

This invention provides a process for preparing an alkylsulfinyl 2-phenylimidazo[4,5-c]pyridine of the formulae

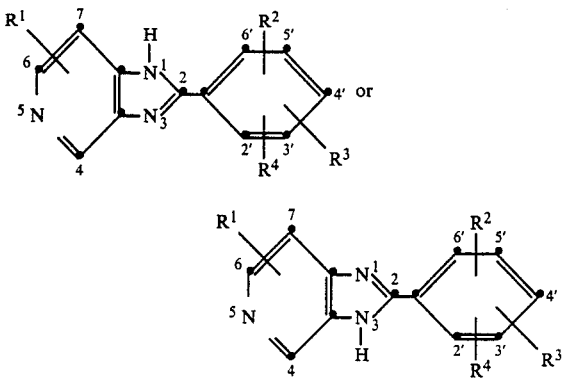

wherein:

$R^1$ is hydrogen, $C_1$–$C_4$ alkyl, $C_1$–$C_4$ alkoxy, or halogen;

$R^3$ is $C_1$–$C_4$ alkylsulfinyl in either the 2', 4', or 6' position;

$R^2$ and $R^4$ independently are hydrogen, hydroxy, halo, cyano, trifluoromethyl, $C_1$–$C_4$ alkyl, $C_1$–$C_4$ alkoxy, $C_2$–$C_4$ alkenyloxy, $C_2$–$C_4$ alkynyloxy, $C_1$–$C_4$ hydroxyalkyloxy, cyanomethoxy, amino, mono- or di-$C_1$–$C_4$ alkylamino, comprising reacting an N-(3-amino-4-pyridinyl)alkylthiobenzamide of the formula

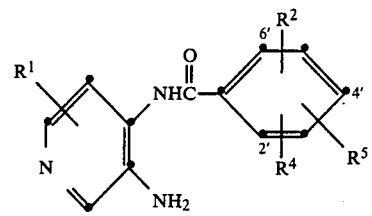

wherein:

$R^1$, $R^2$ and $R^4$ are as defined above; and $R^5$ is $C_1$–$C_4$ alkylthio in either the 2', 4', or 6' position, with an oxidizing agent in a lower alkanoic acid solvent at a temperature of about $-20°$ C. to about 50° C.

A preferred group of compounds which can be prepared by the present process are those wherein $R^1$ and $R^4$ are each hydrogen, and $R^2$ is hydrogen, $C_1$–$C_4$ alkyl, $C_1$–$C_4$ alkoxy, or halogen.

The most preferred compound which can be prepared by the present process is 2-[2-methoxy-4-(methylsulfinyl)phenyl]imidazo[4,5-c]pyridine, a potent inotropic agent.

DETAILED DESCRIPTION OF THE INVENTION

The process of the present invention can be used to produce alkylsulfinyl substituted 2-phenylimidazo[4,5-c]pyridines such as those described in European Patent Application Nos. 93,593 of Robertson et al; 79,083 of King et al; and 72,926 of Jones et al.

The claimed process may be conducted by first mixing an alkylthio substituted N-(3-amino-4-pyridinyl)-benzamide in a lower alkanoic acid. The 3-amino-4-pyridinylbenzamide starting materials employed are either commercially available, known in the literature, or can be prepared by methods known in the art. Suitable lower alkanoic acids are those which exist in liquid form at temperatures between about $-20°$ C. and about 50° C. and atmospheric pressure. Examples of acceptable alkanoic acids are $C_1$–$C_8$ alkanoic acids such as formic acid, acetic acid, propionic acid, n-butyric acid, iso-butyric acid, valeric acid, hexanoic acid, heptanoic acid, and octanoic acid. A preferred lower alkanoic acid is acetic acid. The concentration of starting material in the alkanoic acid is not critical, but it is preferred to employ a sufficient amount of acid solvent to keep the benzamide in solution throughout the reaction.

An oxidizing agent is added to the alkanoic acid mixture. The oxidizing agent generally is employed in approximately 10% to 20% molar excess of the benzamide, with a 16% molar excess being the preferred quantity. Suitable oxidizing agents include hydrogen peroxide and organic peracids such as performic acid, peracetic acid, or m-chloroperbenzoic acid. Hydrogen peroxide is preferred as it allows the reaction to proceed smoothly at about 20° C. to 30° C. without excessive over oxidation to the alkylsulfonyl compound.

The oxidizing agent may be immediately added to the alkanoic acid mixture. Once the oxidizing agent is added to the reaction mixture the temperature will generally begin to rise as the alkylthiol group on the N-(3-amino-4-pyridinyl)benzamide is oxidized to the corresponding alkylsulfinyl group. Desired reaction temperatures are within the range of about −20° C. to about 50° C., with a preferred range being about 20° C. to about 30° C. The reaction temperature should be kept below about 50° C. in order to minimize over oxidation to the alkylsulfonyl compound. The precise temperature at which the reaction is conducted, while not critical, is somewhat dependent on the freezing point of the lower alkanoic acid chosen.

Alternatively, the alkanoic acid mixture may be heated to about 60° C. for up to about 8 hours in order to partially cyclize the alkylthio substituted N-(3-amino-4-pyridinyl)benzamide before the oxidizing agent is added. Once the desired degree of cyclization is achieved, the oxidizing agent is added to hasten complete cyclization, as well as to oxidize the alkylthio group to the required alkylsulfinyl group. The oxidizing agent is added by cooling the reaction mixture to the desired reaction temperature and then adding the oxidizing agent. Once again, the reaction temperature should be kept below about 50° C. in order to minimize over oxidation to the alkylsulfonyl compound.

The process of the present invention is substantially complete after about 6 to 48 hours when conducted at temperatures in the range of about −20° C. to about 50° C. The progress of the reaction can be followed, if desired, by standard high performance liquid chromatography (HPLC) analytical techniques in order to determine when the reaction is substantially complete.

Once the process is substantially complete, the product may be isolated if desired by neutralizing the reaction mixture, for example by adding a suitable base such as sodium bisulfite. The volatile organic constituents are preferably removed by evaporation under reduced pressure. The product generally solidifies and can be isolated by vacuum filtration to afford the desired compound in good purity and high yield.

Alternatively, the product may be isolated, if desired, by adding isopropanol containing a small amount of authentic alkylsulfinyl 2-phenylimidazo[4,5-c]pyridine acetate crystals to serve as seeds, and then cooling the mixture to about 0° C. The product generally crystallizes as the acetate salt and can be isolated by vacuum filtration to afford the desired compound in good purity and high yield.

The alkylsulfinyl 2-phenylimidazo[4,5-c]pyridines produced by the present process are useful as orally effective positive inotropic agents which have minimal effects on blood pressure and heart rate. The compounds also possess vasodilitation, bronchodilation and anticoagulant activities.

The following Examples illustrate specific aspects of the present invention. The Examples are not intended to limit the scope of the present process in any respect and should not be so construed.

EXAMPLE 1

2-[2-methoxy-4-(methylsulfinyl)phenyl]-1(3)H-imidazo[4,5-c]pyridine monohydrochloride To a 250 ml three-neck round bottom flask charged with 14.45 g (0.05 mole) of N-(3-amino-4-pyridinyl)-2-methoxy-4-methylthiobenzamide dissolved in 80 ml of acetic acid were added 5.73 g of 30% hydrogen peroxide. The hydrogen peroxide was added dropwise over a period of five minutes. After addition of the hydrogen peroxide, the reaction mixture was cooled to about 25° C. and stirred for 48 hours, after which time the reaction, as evidenced by HPLC analysis, was substantially complete. At that time, 0.95 g of sodium bisulfite were added to the reaction flask, and the mixture was stirred for 15 minutes. The solution was concentrated to a slurry by removal of the acetic acid using vacuum distillation.

Water (65 ml) and activated carbon (1.4 g) were added to the slurried solution. The resulting mixture was stirred at room temperature for about 2 hours and then filtered through a hyflo pad. The filter cake was washed with 10 ml of water.

The filtrate was mixed with 9.5 ml of concentrated HCl, and then further diluted by addition of 590 ml of isopropanol. The resulting solution was seeded with authentic product compound, stirred at 5° C. for about 3 hours, and then refrigerated overnight.

Following refrigeration the mixture was filtered. The filter cake was dried in a vacuum oven at 40° C. to provide 13.02 g of 2-[2-methoxy-4-(methylsulfinyl)-phenyl]-1(3)H-imidazo[4,5-c]pyridine monohydrochloride.

The water content of the product was determined by Karl Fisher analysis to be 9.62%, providing a total yield of imidazopyridine monohydrochloride of 72.7%. This product assayed 98.84% purity, when compared to reference standards using the HPLC assay discussed below.

The assay samples were dissolved in an internal standard solution consisting of 0.7 mg of 2-naphthalene sulfonic acid sodium salt per ml of an elution solvent comprised of 400 parts of acetonitrile, 100 parts of tetrahydrofuran, 21 parts of glacial acetic acid and 1479 parts of water. The column was eluted with the elution solvent listed above containing 2.2 g of 1-heptane sulfonic acid sodium salt. The column employed was a Whatman Partisil PXS 5/25 ODS. The detector had a wavelength of 320 nm, the column flow rate was 1.0 ml/min, the injection volume was 20 μl and the column temperature was ambient. Three samples were assayed for each compound, and the average which was taken was ±1.9% of the true value at a 95% confidence level.

Assaying the product material by gradient HPLC indicated that less than 0.5% had over oxidized to the 2-[2-methoxy-4-(methylsulfonyl)phenyl]-1(3)H-imidazo[4,5-c]pyridine monohydrochloride compound.

EXAMPLE 2

2-[2-methoxy-4-(methylsulfinyl)phenyl-1(3)H-imidazo[4,5-c]pyridine monohydrochloride N-(3-amino-4-pyridinyl)-2-methoxy-4-methylthiobenzamide (7.24 g, 0.025 mole) was suspended in 40 ml of acetic acid. The solution was heated to about 60° C. and stirred for 4 hours. At that time the solution was cooled to 18° C. and 3.28 g of 30% hydrogen peroxide were added dropwise over a period of five minutes.

After addition of the hydrogen peroxide the reaction mixture was stirred for 29 hours at room temperature (25° C.), after which time the reaction, as evidenced by HPLC analysis, was substantially complete.

Isopropanol (120 ml), seeded with authentic 2-[2-methoxy-4-(methylsulfinyl)phenyl-1(3)H-imidazo[4,5-c]pyridine acetate crystals, was added and the mixture cooled to about 0° C. for 3 hours. After 3 hours the mixture was filtered and the filter cake, comprising the imidazopyridine acetate salt, was washed with 10 ml of a 1:3 acetic acid/isopropanol mixture.

The acetate salt was dissolved in 32 ml of water and treated with 0.66 g of activated carbon. The resulting mixture was stirred at room temperature (25° C.) for about 1 hour, then filtered through a hyflo pad. The filter cake was washed with 6 ml of water and 60 ml of isopropanol successively.

The filtrate was mixed with 4.1 ml of concentrated HCl, then further diluted by the addition of 200 ml isopropanol. The resulting solution was seeded with authentic product compound, stirred at 5° C. for about 3 hours, and then filtered. The filter cake, washed with 10 ml of a 7:1 isopropanol/water mixture, was dried in a vacuum oven at 30° C. to provide 5.76 g of 2-[2-methoxy-4-(methylsulfinyl)phenyl]-1(3)H-imidazo[4,5-c]pyridine monohydrochloride.

The water content of the product was determined by Karl Fisher analysis to be 17.0%, providing a total yield of imidazopyridine monohydrochloride of 59.0%. This product assayed 99.5% purity using the assay procedure discussed in Example 1.

Assaying the product material by gradient HPLC indicated that less than 0.25% had over oxidized to the 2-[2-methoxy-4-(methylsulfonyl)phenyl]-1(3)H-imidazo[4,5-c]pyridine monohydrochloride compound.

We claim:

1. A process for preparing an alkylsulfinyl 2-phenylimidazo[4,5-c]pyridine of the formulae

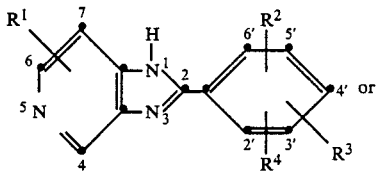 or 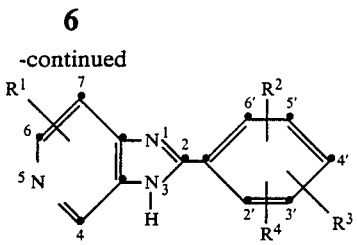

wherein:
 $R^1$ is hydrogen, $C_1$–$C_4$ alkyl, $C_1$–$C_4$ alkoxy, or halogen;
 $R^3$ is $C_1$–$C_4$ alkylsulfinyl in either the 2', 4', or 6' position;
 $R^2$ and $R^4$ independently are hydrogen, hydroxy, halo, cyano, trifluoromethyl, $C_1$–$C_4$ alkyl, $C_1$–$C_4$ alkoxy, $C_2$–$C_4$ alkenyloxy, $C_2$–$C_4$ alkynyloxy, $C_1$–$C_4$ hydroxyalkyloxy, cyanomethoxy, amino, mono- or di-$C_1$–$C_4$ alkylamino, comprising reacting an N-(3-amino-4-pyridinyl)alkylthiobenzamide of the formula

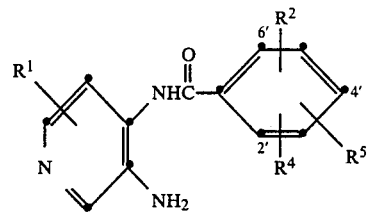

wherein:
 $R^1$, $R^2$ and $R^4$ are as defined above; and
 $R^5$ is a $C_1$–$C_4$ alkylthio in either the 2', 4', or 6'-position, with an oxidizing agent in a lower alkanoic acid solvent at a temperature of about −20° C. to about 50° C.

2. A process of claim 1 employing hydrogen peroxide, or an organic peracid selected from peracetic acid, performic acid, and m-chloroperbenzoic acid.

3. The process of claim 1 employing hydrogen peroxide.

4. A process of claim 2 employing an (N-3-amino-4-pyridinyl)alkylthiobenzamide wherein: $R^1$ and $R^4$ are hydrogen; $R^5$ is $C_1$–$C_4$ alkylthio; and $R^2$ is hydrogen, $C_1$–$C_4$ alkyl, $C_1$–$C_4$ alkoxy, or halogen.

5. A process of claim 2 employing an (N-3-amino-4-pyridinyl)alkylthiobenzamide wherein: $R^1$ and $R^4$ are hydrogen; $R^5$ is methylthio; and $R^2$ is hydrogen, methyl, methoxy, or halogen.

6. The process of claim 2 wherein N-(3-amino-4-pyridinyl)-2-methoxy-4-methylthiobenzamide is converted to 2-[2-methoxy-4-(methylsulfinyl)phenyl]imidazo[4,5-c]pyridine.

* * * * *